United States Patent [19]

Onodera et al.

[11] Patent Number: 5,580,542
[45] Date of Patent: Dec. 3, 1996

[54] METHOD OF TESTING FOR NEPHRITIS

[75] Inventors: Chikau Onodera; Hiromi Yoshihara, both of Tokyo; Mikiro Yanaka, Matsudo, all of Japan

[73] Assignee: Kureha Kagaku Kogyo K.K., Tokyo, Japan

[21] Appl. No.: 460,944

[22] Filed: Jun. 5, 1995

Related U.S. Application Data

[62] Division of Ser. No. 327,827, Oct. 24, 1994, abandoned.

[30] Foreign Application Priority Data

Oct. 29, 1993 [JP] Japan .................................. 5-292475

[51] Int. Cl.$^6$ .................................................. G01N 33/493
[52] U.S. Cl. .......................... 424/9.1; 514/114; 514/381; 514/535; 514/562; 514/563; 514/649
[58] Field of Search ..................................... 514/114, 381, 514/535, 562, 563, 649; 424/9.1

[56] References Cited

PUBLICATIONS

Pacifici et al., *Xenobiotica*, 1988, vol. 18, No. 7, 849–856.
Cribb et al., *The Journal of Pharmacology and Experimental Therapeutics*, 259: 1241–1246 (1991).

*Primary Examiner*—José G. Dees
*Assistant Examiner*—Joseph M. Conrad, III
*Attorney, Agent, or Firm*—Lowe, Price, LeBlanc & Becker

[57] ABSTRACT

Disclosed is an acetyltransferase activity measuring agent which contains an arylamine derivative. As the arylamine derivative, sodium p-aminohippurate can be used preferably. Use of the acetyltransferase activity measuring agent of this invention permits a simple and safe diagnosis of the progress of the pathema of nephritis, which is accompanied by a mesangial proliferative lesion, or renal insufficiency. Furthermore, the scattering of measured values is small, thereby assuring an accurate diagnosis.

4 Claims, 1 Drawing Sheet

Concentration of PAH in Blood

Concentration of AcPAH in Blood

METHOD OF TESTING FOR NEPHRITIS

This application is a division of application Ser. No. 08/327,827 filed Oct. 24, 1994 now abandoned.

BACKGROUND OF THE INVENTION

1. Field of the Invention

This invention relates to an acetyltransferase activity measuring agent which comprises an arylamine derivative.

2. Description of the Related Art

Tests of renal excretory function by measuring clearance are conventionally known as renal function tests. As one of these tests, creatinine clearance which makes use of creatinine as an endogenous substance is often used clinically to test the physical function in terms of glomerular filtration rate (GFR). In the renal function test by measuring creatinine clearance, however, urine required for the test is preferably collected over 24 hours. The renal function test by creatinine clearance is therefore accompanied by the drawbacks that a substantial time is needed until test results are obtained, the test tends to be affected by the quantity of urine, body movements and the like, and measured values are prone to scattering.

Further, to check the renal plasma flow (RPF), one of parameters of physical function of the kidneys, PAH clearance using p-aminohippuric acid (PAH) is also employed. Although PAH has the merits that it has safety to the human body and can be promptly excreted into urine when administered by intravenous infusion, PAH involves the problems that it is laborious and inflicts pain on subjects because upon conducting a test, continuous intravenous infusion is performed and a catheter is inserted into the bladder to collect urine at predetermined time points.

Incidentally, many of nephritides which cause lowering in renal function are mesangial proliferative, typified by immunoglobulin A (IgA) nephritis. Nephritis having a mesangial proliferative lesion is progressive and has high possibility of resulting in renal insufficiency and the need for dialysis. To determine and diagnose such nephritis, histopathological findings of kidney tissue obtained by biopsy are indispensable. Kidney biopsy and such histopathological findings, however, can be conducted only at a hospital equipped with facilities therefor. To conduct kidney biopsy, a subject has to be hospitalized. Moreover, there is the potential risk that upon biopsy, one or more blood vessels may be damaged or the subject may be affected by an infectious disease.

On the other hand, N-acetylation of an aromatic amine in the human body is a reaction in which acetyltransferase, an enzyme in the body, takes part. It has been reported that acetyltransferase activity is observed on excised organs such as kidneys and livers and also on white blood cells [G. M. Pacifici et al., Xenobiotica 18(7), 849–856 (1988), A. E. Cribb et al., J. Pharmacol. Exp. Ther., 259(3), 1241–1246 (1991)].

SUMMARY OF THE INVENTION

An object of the present invention is therefore to overcome the above-described problems in the conventional tests of physical function of the kidneys.

Described specifically, an object of the present invention is to provide an acetyltransferase activity measuring agent, which enables one to conduct in a short time a simple and safe diagnosis of the development of nephritis, which is accompanied by a mesangial proliferative lesion, or renal insufficiency or the progress of its pathema and further to obtain measurement values having a small scattering.

The present inventors were interested in the participation of acetyltransferase in the N-acetylation of an aromatic amine and as a result of an extensive investigation, have found by an in-vitro system the existence of this acetyltransferase activity in mesangial cells of a kidney tissue, leading to the completion of the present invention.

The acetyltransferase activity measuring agent according to this invention features inclusion of an arylamine derivative.

DETAILED DESCRIPTION OF PREFERRED EMBODIMENTS

Figure 1:
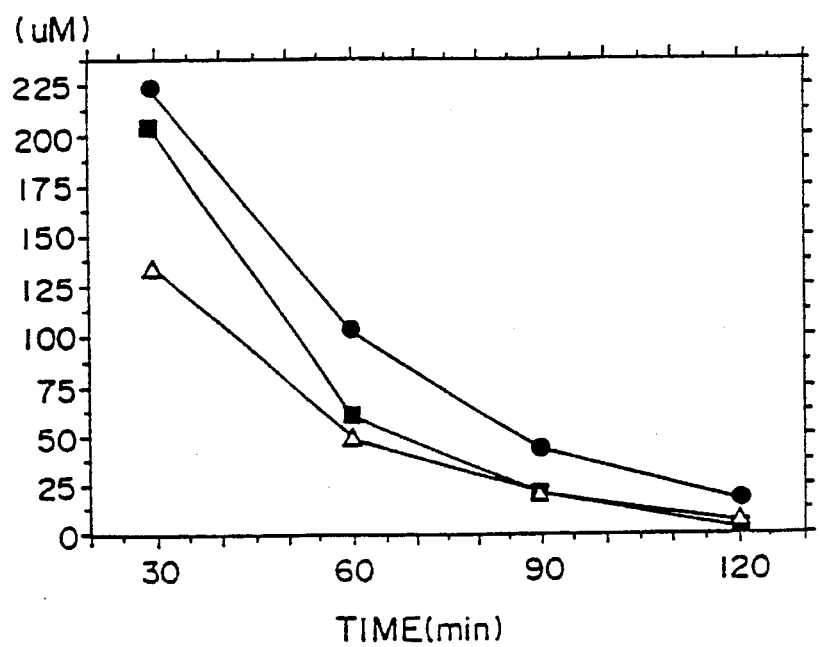
FIG. 1 is a plot of the relationship between the concentration of PAH in blood versus time in rats.

In the present invention, the acetyltransferase activity measuring agent is used in the form of an aqueous solution, suspension or emulsion of the arylamine derivative for injection or infusion. This measuring agent is stored in bottles, ampoules or the like.

Examples of the arylamine derivative in the present invention include p-substituted aniline derivatives by the following formula and pharmaceutically acceptable salts thereof:

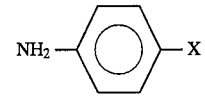

wherein X represents —COOH, —CONH$_2$, —CONHCH$_3$, —CON(CH$_3$)$_2$, —CONHCH$_2$COOH, —CONH—CH(—R)COOH (R: a side chain group of a proteinaceous amino acid), —CONH(CH$_2$)$_n$COOH (n: 2 to 3), —SO$_3$H, —SO$_2$NH$_2$, —SO$_2$NHCH$_3$, —SO$_2$N(CH$_3$)$_2$, —SO$_2$NHCH$_2$COOH, —SO$_2$NH—CH(—R) COOH (R: a side chain group of a proteinaceous amino acid), —SO$_2$NH(CH$_2$)$_n$COOH (n: 2 to 3), PO$_3$H, —OH, —OCOCH$_3$, —O-sulfonate ester, —O-glucuronate ester, —COCH$_2$NH$_2$, 1-tetrazol-5-yl, or —(CH$_2$)$_n$-Y (Y: same as X, n: 1 to 2).

Examples of the side chain groups of the proteinous amino acids represented by R in the above formula include: methyl group (the side chain group of alanine), isopropyl group (the side chain group of valine), isobutyl group (the side chain group of leucine), s-butyl group (the side chain group of isoleucine), methylthioethyl group (the side chain group of methionine), phenylmethyl group (the side chain group of phenylalanine), indolylmethyl group (the side chain group of tryptophan), hydroxymethyl group (the side chain group of serine), hydroxyethyl group (the side chain group of threonine), carbamoylmethyl group (the side chain group of asparagine), carbamoylethyl group (the side chain group of glutamine), carboxymethyl group (the side chain group of aspartic acid), carboxyethyl group (the side chain group of glutamic acid), sulfhydrylmethyl (the side chain group of cysteine), phenoxymethyl group (the side chain group of tyrosine), imidazolylmethyl group (the side chain group of histidine), aminobutyl group (the side chain group of lysine), and guanididopropyl group (the side chain group of arginine).

Among the above-exemplified arylamine derivatives, derivatives of p-aminobenzoic acid are preferred. In particular, p-aminobenzoic acid and its water-soluble salts, such as its sodium salt, as well as p-aminohippuric acid and its water-soluble salts, such as its sodium salt 3 can be used as preferred ones. In the case of sodium p-aminohippurate, for example, a concentration of 3 mg/ml to 30 mg/ml is easy for use and a dose of 1 mg/kg to 200 mg/kg is preferred.

According to the recent finding by the present inventors, the N-acetylating ability of the living body changes in the case of nephritis, which is accompanied by a mesangial proliferative lesion, or renal insufficiency and varies as the pathema of the kidney progresses because as has been confirmed in an in-vitro system as described above, there is acetyltransferase activity in mesangial cells of kidney tissue.

Since acetyltransferase takes part in the N-acetylation of an aromatic amine, use of the acetyltransferase activity measuring agent according to this invention makes it possible to diagnose development of the pathema of nephritis, which is accompanied by a mesangial proliferative lesion, or renal insufficiency or the degree of its progress. When the acetyltransferase activity measuring agent according to this invention is administered to the body, preferably intravenously injected, it is excreted into urine in a short time. Subsequent quantitative analysis of the arylamine derivative and the N-acetylated arylamine derivative in urine makes it possible to ascertain the degree of N-acetylating ability of the mesangial cells. Accordingly, it has become possible to simply and safely diagnose in a short time the development of the pathema of nephritis, which is accompanied by a mesangial proliferative lesion, or renal insufficiency or the degree of its progress. Further, scattering of their measurement values in blood and urine is small so that the activity of acetyltransferase can be measured with good accuracy.

EXAMPLES

Test 1

In this test, the activity of acetyltransferase was evaluated by an in-vitro experiment with respect to p-aminobenzoic acid.

The left and right kidneys of 7 weeks-old Sprague-Dawley female rats were excised. After the renal cortices were shredded, mesangial cells were prepared by the Sieving's method. For the sake of comparison, "A7r5" (trade name, derived from fetal thoracic aortic smooth muscle), "Clone 9" (trade name. derived from liver), "$H_9c2$ (2-1)" (trade name, derived from cardiorhabdium), "IEC-18" (trade name, derived from the small intestine) and "NRK-52E" (trade name, derived from epithelial cells of renal tubule), all products of Flow Corp., U.S.A., were used as cells derived from rats.

Using as a culture medium "RPMI-1640" (trade name; product of Flow Corp.; U.S.A.) added with fetal bovine serum (product of GIBCO Corp.) whose concentration was finally 10% in the medium, those cells were cultured in a 5% $CO_2$ incubator. Since the p-amionbenzoic acid contained in RPMI-1640 was converted to p-acetamidobenzoic acid by the above culture, detection was conducted with respect to the p-acetamidobenzoic acid so converted.

Namely, 2 ml of each culture medium after the lapse of 2 to 3 days since its culture were subjected to centrifugal ultrafiltration to eliminate proteins. One ml of the filtrate was added with 30 µl of 1N hydrochloric acid to adjust the pH to pH 1. Added next were 10 µg of p-pentylbenzoic acid, as an internal standard, and 0.5 g NaCl. The resulting mixture was shaken three times together with 3 ml portions of ethyl acetate to conduct liquid/liquid extraction of the organic acid component. After the extract was dried under a nitrogen gas stream, 40 µl of N,O-bis(trimethylsilyl)trifluoroacetamide and 10 µl of trimethylchlorosilane were added. The resulting mixture was stirred at 60° C. for 1 hour so that the organic acid component was trimethylsilylated. The trimethylsilylated organic acid component was then detected by gas chromatography mass spectrometry. The activity of acetyltransferase was evaluated by the relative height of a peak corresponding to p-acetamidobenzoic acid. The results are presented in Table 1. The following evaluation standard was employed:–: smaller than 50,000,+: 50,000 or greater but smaller than 500,000, ++: 500,000 or greater, all in terms of abundance.

TABLE 1

| Cells | Evaluation results |
| --- | --- |
| Mesangial cells | ++ |
| A7r5 | – |
| Clone 9 | – |
| H9c2(2-1) | – |
| IEC-18 | – |
| NRK-52E | – |

From the results of Table 1, mesangial cells have been confirmed to have N-acetyltransferase activity to p-aminobenzoic acid.

Test 2

In this test, an investigation was conducted about the relationship, if any, between the degree of ligature of the renal artery, which serves as an index for the degree of progress of the pathema of a kidney disease, and the concentration ratio of p-acetyl-aminohippuric acid (AcPAH) to p-aminohippuric acid (PAH) in urine.

Nine Sprague-Dawley male rats, who were 12 weeks old had a body weight of 400–450 g, were used. Depending on whether the renal arterial carina ligating method was applied and if so, how tight the ligating method as applied, the rats were divided into three groups, each consisting of three of the rats, that is, a sham-operation group (i.e., control), a ½ renal arterial ligature group (only one kidney was functioning) and a ⅚ renal arterial ligature group. On the 37th day after the operation, an aqueous solution of 40 mg of sodium p-aminohippurate (Na-PAH) in 200 µl of distilled water was administered as a single shot to the jugular vein of each rat under anesthesia with ethyl ether. The rat was then immediately placed in metabolism test cage, and urine was collected over 24 hours. The concentrations of AcPAH and PAH in urine were analyzed by high-performance liquid chromatography in a manner to be described subsequently herein, whereby the ratio of AcPAH to PAH (AcPAH/PAH) was determined.

Namely, 150 µl of methanol, which contained 1 µg of vanillic acid as an internal standard substance, were added to 50 µl of fivefold dilute urine. After the resulting mixture was stirred and centrifuged, the supernatant was collected and was subjected to filtration by centrifugation. By high-performance liquid chromatography, 10 µl of the supernant so obtained were quantitatively analyzed under the following analysis conditions:

Analysis Conditions:

Column: "Unisil Pack 250B" (trade name, product of GL Science Inc.)

Mobile phase: water/acetic acid/acetonitrile=93.5/0.5/6 (pH 3, approximately)

Flow rate: 1.5 ml/min

Column oven temperature: 40° C.

UV: 270 nm

The results are presented below in Table 2.

TABLE 2

| Sham-operation group (n = 3) | 1/2 Renal arterial ligature group (n = 3) | 5/6 Renal arterial ligature group (n = 3) |
|---|---|---|
| 0.132 | 0.144 | 0.236 |
| 0.121 | 0.153 | 0.242 |
| 0.123 | 0.141 | 0.272 |
| Ave. 0.125 | 0.146 | 0.250 |

From the results of Table 2, the urinal AcPAH/PAH ratio has been confirmed to increase as the pathema of the kidneys becomes severer.

Test 3

In this test, an investigation was conducted about the time-dependent stability of test results which were obtained using an acetyltransferase activity measuring agent according to the present invention.

Three Sprague-Dawley male rats, who were 13 weeks old and had a body weight of 410–470 g, were used. An aqueous solution of 40 mg of sodium p-aminohippurate (Na-PAH) in 200 µl of distilled water was administered as a single shot to the jugular vein of each rat under anesthesia with ethyl ether. The rat was then immediately placed in metabolism test cage, and urine was collected over 24 hours. The concentrations of AcPAH and PAH in urine were analyzed as in Test 2, whereby the AcPAH/PAH ratio was determined. The above test was repeated 7 times on different days so that its average value, standard deviation (S.D.) and coefficient of variations (C.V.) were determined.

As a comparative example, the levels of blood and urine creatinine were also measured to determine the creatinine clearance (CCr). Incidentally, the measurement of the creatinine levels was conducted by the Rate's colorimetic analysis. "Creatinine Analyzer 2" (trade name, manufactured by Beckman Instruments, Inc.) was used.

The results are presented in Table 3.

TABLE 3

| Animal | Item of measurement | Ave. S.D | C.V |
|---|---|---|---|
| Rat #1 | Urinal AcPAH/PAH | 0.125 ± 0.0117 | 9.4% |
| | CCr | 2.450 ± 0.493 | 20.5% |
| Rat #2 | Urinal ACPAH/PAH | 0.100 ± 0.0086 | 8.6% |
| | CCr | 1.765 ± 0.243 | 13.8% |
| Rat #3 | Urinal ACPAH/PAH | 0.131 ± 0.00598 | 4.6% |
| | CCr | 2.234 ± 0.247 | 11.1% |

As is evident from the results of Table 3, the measurement data of the AcPAH/PAH ratio have smaller variations compared with the measurement data of the creatinine clearance (CCr). It is therefore appreciated that the method making use of the acetyltransferase activity measuring agent of this invention is excellent in the stability with days and provides measurement data having small variations. Test 4

In the test, the rate of secretion of an acetyltransferase activity measuring agent according to this invention into urine was tested.

Three Sprague-Dawley male rats, who were 29 weeks old and had a body weight of 610–660 g, were used. An aqueous solution of 40 mg of sodium p-aminohippurate (Na-PAH) in 200 µl of distilled water was administered as a single shot to the jugular vein of each rat under anesthesia with ethyl ether. Upon elapsed time of 30 minutes, 60 minutes, 90 minutes and 120 minutes, the concentrations of PAH and AcPAH in blood were measured by high-performance liquid chromatography. Serum was used in an amount of 50 µl each time. The pretreatment method and analysis conditions were the same as in Test 2. The results are presented in FIGS. 1 and 2.

Figure 2:
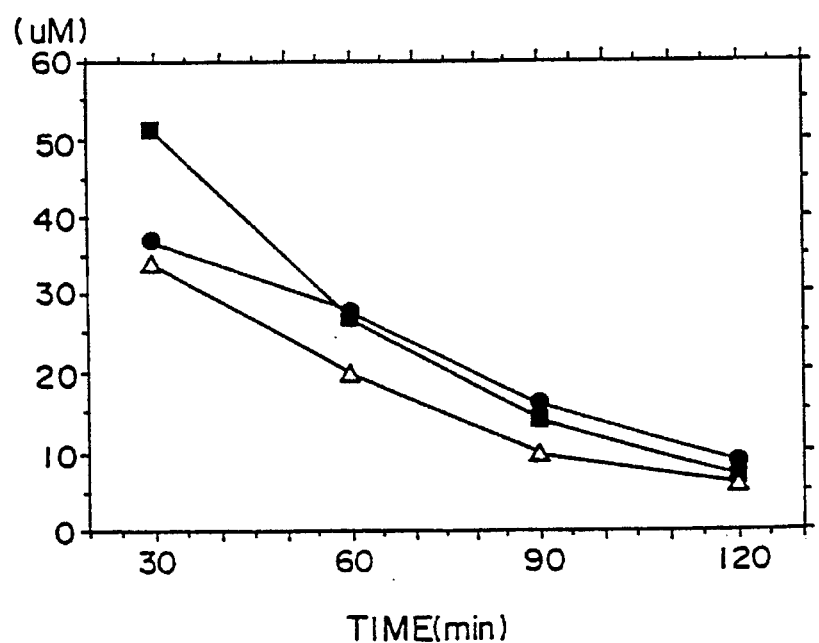
FIG. 2 is a plot of the relationship between the concentration of AcPAH in blood versus time in rats.

As is apparent from FIGS. 1 and 2, it is appreciated that PAH is substantially eliminated from blood in 120 minutes after the administration and its metabolite, AcPAH, also becomes low in concentration in 120 minutes after the administration and is promptly secreted into urine. This indicates that the development or the degree of progress of the pathema of nephritis, which is accompanied by a mesangial proliferative lesion, or renal insufficiency can be diagnosed only by administering an acetyltransferase activity measuring agent of this invention into blood by single injection or infusion and collecting urine upon an elapsed time of 2–3 hours.

What is claimed is:

1. A method of testing for nephritis which is accompanied by a mesangial proliferative lesion or renal insufficiency in a patient suspected of having nephritis, by administering to said patient or to a culture of excised kidney cells from said patient, an aqueous solution, suspension or emulsion of a p-substituted aniline or a pharmaceutically acceptable salt thereof having the following formula:

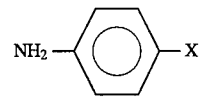

wherein X represents —COOH, —CONH$_2$, —CONHCH$_3$, —CON(CH$_3$)$_2$, —CONHCH$_2$COOH, —CONHC(R)HCOOH, —CONH(CH$_2$)$_{2-3}$COOH, —SO$_3$H, —SO$_2$NH$_2$, —SO$_2$NHCH$_3$, —SO$_2$N(CH$_3$)$_2$, —SO$_2$NHCH$_2$COOH, —SO$_2$NHC(R)HCOOH, —SO$_2$NH(CH$_2$)2-3COOH, —PO$_3$H, —OH, —OCOCH$_3$, —O-sulfonate ester, —O-glucuronate ester, —COCH$_2$NH$_2$, 1-tetrazol-5-yl, and —(CH$_2$)$_{1-2}$-Y, wherein Y is the same as X and R represents a side chain of a proteinaceous amino acid; measuring the amount of N-acetylated p-substituted aniline derivative produced and comparing this value against a pre-established standard to evaluate the activity of acetyltransferase in the patient and thereby to determine whether a nephritic condition is indicated.

2. The method of claim 1 wherein the substituted aniline is p-aminohippuric acid or the sodium salt thereof.

3. The method of claim 1 wherein the substituted aniline is p-aminobenzoic acid or the sodium salt thereof.

4. The method of claim 1 wherein the activity of acetyltransferase is evaluated by measuring the amount of N-acetylated aniline compound present in the patient's blood and/or urine.

* * * * *